United States Patent
Edwards (10) Patent No.: US 7,812,602 B2
(45) Date of Patent: Oct. 12, 2010

(54) MULTIPLE ECHO TRAIN INVERSION

(75) Inventor: Carl M. Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 495 days.

(21) Appl. No.: 11/781,522

(22) Filed: Jul. 23, 2007

(65) Prior Publication Data

US 2007/0290684 A1    Dec. 20, 2007

Related U.S. Application Data

(63) Continuation of application No. 11/037,834, filed on Jan. 18, 2005, now abandoned.

(51) Int. Cl.
*G01V 3/00* (2006.01)
(52) U.S. Cl. ...................... 324/303; 324/306
(58) Field of Classification Search ............... 324/303, 324/306
See application file for complete search history.

(56) References Cited

U.S. PATENT DOCUMENTS

| | | | |
|---|---|---|---|
| 5,023,551 A | 6/1991 | Kleinberg et al. | 324/303 |
| 5,585,720 A | 12/1996 | Edwards | 324/309 |
| 6,069,477 A | 5/2000 | Chen et al. | 324/303 |
| 6,163,153 A | 12/2000 | Reiderman et al. | 324/314 |
| 6,232,778 B1 * | 5/2001 | Speier et al. | 324/303 |
| 6,255,819 B1 * | 7/2001 | Day et al. | 324/303 |
| 6,331,775 B1 | 12/2001 | Thern et al. | 324/303 |
| 6,348,792 B1 | 2/2002 | Beard et al. | 324/303 |
| 6,377,042 B1 | 4/2002 | Menger et al. | 324/303 |

FOREIGN PATENT DOCUMENTS

WO    WO97/34166    9/1997

* cited by examiner

*Primary Examiner*—Louis M Arana
(74) *Attorney, Agent, or Firm*—Mossman Kumar & Tyler PC (57) ABSTRACT

A method for inversion of multiple echo trains with different wait times uses a cutoff times for each of the echo trains for full polarization. Simultaneous inversion is carried out for $T_2$ bins where full polarization exists. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

22 Claims, 6 Drawing Sheets

MULTIPLE ECHO TRAIN INVERSION

CROSS-REFERENCES TO RELATED APPLICATIONS

This application is a continuation of U.S. patent application Ser. No. 11/037,834 filed on Jan. 18, 2005.

BACKGROUND OF THE INVENTION

1. Field of the Invention

This invention is related to methods for acquiring nuclear magnetic resonance (NMR) measurements for determination of petrophysical properties of formations and properties of fluids therein. Specifically, the invention deals with simultaneous inversion of multiple echo trains for processing and interpreting Nuclear Magnetic Resonance (NMR) log data that exhibit relaxation and/or polarization.

2. Description of the Related Art

Nuclear magnetic resonance is used in the oil industry, among others, and particularly in certain oil well logging tools. NMR instruments may be used for determining, among other things, the fractional volume of pore space and the fractional volume of mobile fluid filling the pore space of earth formations. Methods of using NMR measurements for determining the fractional volume of pore space and the fractional volume of mobile fluids are described, for example, in "Spin Echo Magnetic Resonance Logging: Porosity and Free Fluid Index Determination," M. N. Miller et al., Society of Petroleum Engineers paper no. 20561, Richardson, Tex., 1990. Further description is provided in U.S. Pat. No. 5,585,720, of Carl M. Edwards, issued Dec. 17, 1996 and having the same assignee as the present application, entitled "Signal Processing Method For Multiexponentially Decaying Signals And Applications To Nuclear Magnetic Resonance Well Logging Tools." The disclosure of that patent is incorporated herein by reference.

Figure 1:
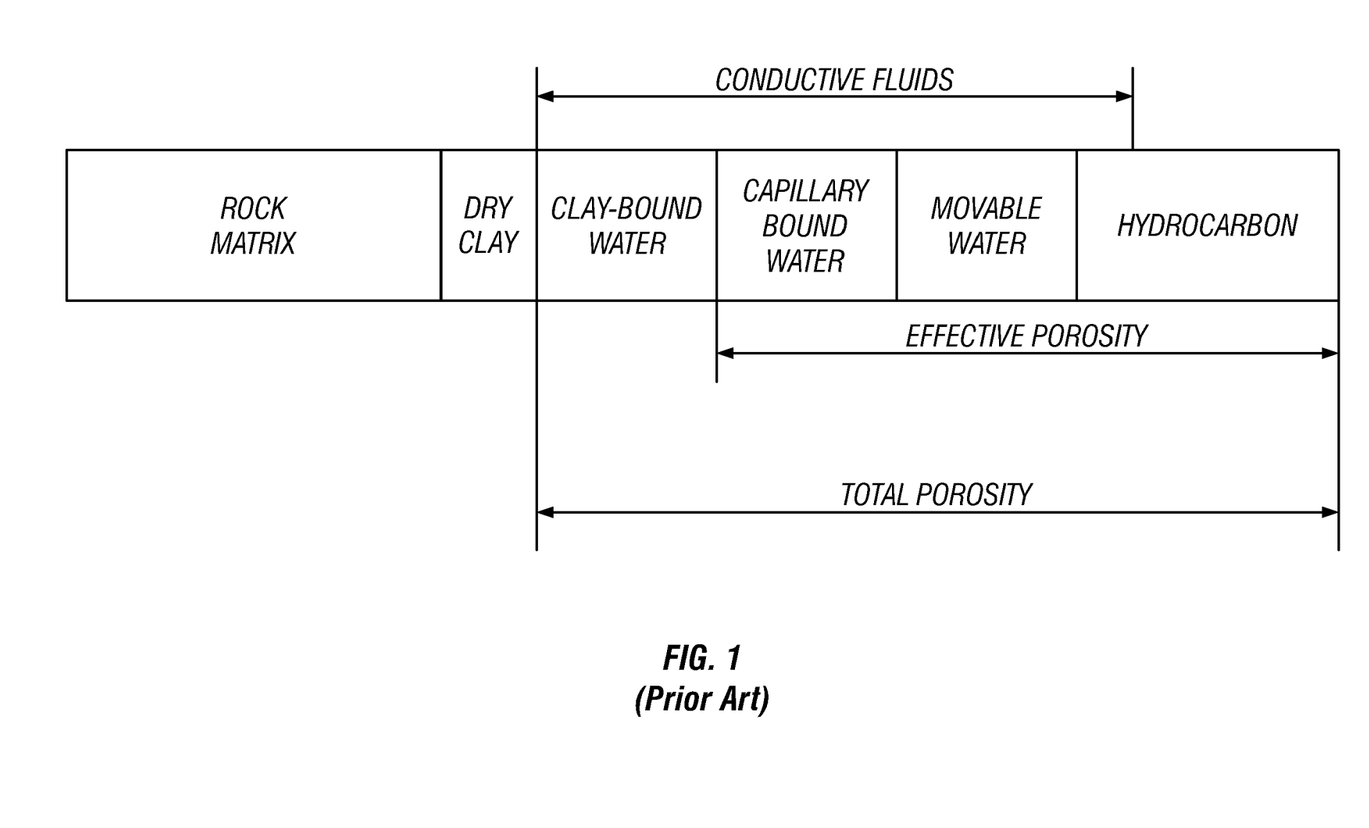
FIG. 1 (prior art) shows the different constituents of a fluid filled rock.

Deriving accurate relaxation spectra from nuclear magnetic resonance (NMR) data from logging subterranean formations is critical to determining total and effective porosities, irreducible water saturations, and permeabilities of the formations. U.S. Pat. No. 6,069,477 to Chen et al having the same assignee as the present application discusses the constituents of a fluid saturated rock and various porosities of interest. Referring to FIG. 1, the solid portion of the rock is made up of two components, the rock matrix and dry clay. The total porosity as measured by a density logging tool is the difference between the total volume and the solid portion. The total porosity includes clay-bound water (CBW), capillary bound water (also known as Bulk volume Irreducible or BVI), movable water and hydrocarbons. The effective porosity, a quantity of interest to production engineers, is the sum of the last three components and does not include the clay bound water. Accurate spectra are also essential to estimate the irreducible and the movable fluid volumes; distortion of partial porosity distributions that has been commonly observed for a variety of reasons, affects the estimates of these quantities. The reasons for the distortions to occur are mainly due to poor signal-to-noise ratio (SNR) and poor resolution in the time domain of the NMR data.

The most common NMR log acquisition and core measurement method employs $T_2$ measurements using CPMG (Carr, Purcell, Meiboom and Gill) sequence, as taught by Meiboom and Gill in "Modified Spin-Echo Method for Measuring Nuclear Relaxation Time," Rev. Sci. Instrum. 1958, 29, pp. 688-691. In this method, the echo data in any given echo train are collected at a fixed time interval, the interecho time (TE). Depending on the relaxation rate of the nuclear species under investigation in the underlying system, usually, a few hundred to a few thousand echoes are acquired to sample relaxation decay. Determining a light oil component, which has long relaxation time, requires taking several hundreds of ms of data while determination of CBW, which decays very fast, can be done with echo sequences of as short as a few tens of milliseconds.

There are numerous examples of NMR logging techniques used for obtaining information about earth formations and fluids. In measurement-while-drilling (MWD) operation, measurements are made while the wellbore is being drilled while in wireline logging, measurements are made after a wellbore has been drilled. The logging tools are lowered into the borehole and NMR signals are obtained using different configurations of magnets, transmitter coils and receiver coils. A static magnetic field is produced in the formation using permanent or electro-magnets. The static field aligns nuclear spins within the formation parallel to the static field. A pulsed RF field is applied using a transmitter on the logging tool and the nuclear magnetization signals produced by the pulsed RF field are analyzed to determine formation properties. The prior art shows different radio frequency (RF) pulsing schemes for generating RF fields in the formation. The most commonly used pulsing schemes are variations of the CPMG sequence denoted by $$TW_i, 90_{\pm \pi/2}, (\tau, 180, \tau, echo)_j)_i \quad (1)$$

where TW is a wait time, 90 is a tipping pulse that tips the nuclear spins by an angle substantially equal to 90°, 180 is a refocusing pulse that tips the nuclear spins by an angle substantially equal to 180°, and echo is a spin echo. The time interval between successive refocusing pulses is $2\tau$, the number of echoes is j, and i denotes repetitions of the basic pulse sequence. A variation of the CPMG sequence is taught in U.S. Pat. No. 6,163,153 to Reiderman in which the use of a refocusing pulse with a tipping angle less than 180° is disclosed.

Rig time is expensive, so that the general objective in wireline logging is to obtain interpretable data within as short a time as possible. In MWD logging, on the other hand, no additional rig time is involved. However, when more measurements can be acquired in a given time, the data quality can be improved. The parameters that may be varied are the acquisition frequencies and the number of different frequencies, the tip angles, the wait time, the number of pulses within a CPMG sequence, and the time interval between the pulses. Long wait times are needed for proper evaluation of formation fluids that have long relaxation times, e.g., gas reservoirs while short wait times and/or short pulse spacings are used for evaluating faster relaxing components, e.g., irreducible fluid (BVI) and clay bound water (CBW). For example, U.S. Pat. No. 6,331,775 to Thern et al., having the same assignee as the present application discusses the use of a dual wait time acquisition for determination of gas saturation in a formation. U.S. Pat. No. 5,023,551 to Kleinberg et al discusses the use of CPMG sequences in well logging. U.S. Pat. No. 6,069,477 to Chen et al teaches the use of pulse sequences with different pulse spacings to determine CBW.

NMR fluid typing applications often involve acquiring multiple echo trains to exploit the diffusion and/or polarization contrasts between the water and hydrocarbon phases. Although proven successful in wells where these contrasts are large, the NMR-based techniques are challenging when the contrasts are small. Carbonates generally exhibit smaller NMR surface relaxivity than clastics, which reduces the relaxation time contrast between movable water and light oil.

This difficulty is exacerbated by the small difference in the diffusivities of water and very light oil. In such cases, the methods for processing data are critical and the introduction of a priori information important.

U.S. patent application Ser. No. 10/288,115 of Chen et al., having the same assignee as the present invention and the contents of which are fully incorporated herein by reference, teaches the use of multifrequency NMR acquisition using various combinations of wait times, interecho times in pulse sequences of different lengths in an objective oriented method for formation and reservoir analysis. The objectives of Chen '115 may include formation evaluation, fluid typing, diffusivity determination The pulse sequences taught therein are suitable for use with the present invention. The mention of the Chen '115 application is not intended to be a limitation on the present invention and other types of pulse sequences could be used.

New generation NMR well logging tools can acquire multiple echo trains with different TWs and TEs in a single logging pass. Simultaneously inverting all echo data to obtain the different fluid $T_2$ spectra is a logical method for the processing and interpretation of multiple echo trains acquired with different acquisition parameters. In fact, echo trains acquired with different TEs and TWs can not simply be averaged together to increase the signal-to-noise and inverted because they may exhibit very different $T_2$ decay behaviors. Thus, it is desirable to use an analysis technique that accounts for the different acquisition parameters in the individual echo trains. U.S. patent application Ser. No. 10/435,419 of Chen, having the same assignee as the present invention and the contents of which are incorporated herein by reference, discloses an apparatus and a method of combining echo trains acquired with different parameters. Multiecho sequences are acquired from a first and second region of interest using a first and second radio frequency (RF) pulse sequence. A correction factor depending at least in part on a diffusivity of a fluid in the earth formation is determined, and the first and second multiecho sequences are combined using the correction factor to obtain a combined multiecho sequence. The method taught therein is difficult to extend to multiple echo trains, and the specific problem of small contrasts is not addressed. A similar approach (combining echo trains without gradient variations) is discussed in U.S. Pat. No. 6,377,042 issued to Menger. EP 0886792 to Bonnie et al. discloses a method in which NMR echo signals are acquired with different combinations of TW, TE and field gradient (produced by a gradient coil), and a curve fitting procedure is used to match the resulting signals to a predetermined model. The model itself is limited in scope.

Others have processed multiple echo trains of NMR data by separately inverting them and then by splicing the two separate inversion results. See, for example, U.S. Pat. No. 6,005,389 to Prammer. The methods of splicing generally assume that the ratio $T_1/T_2$ is constant.

There is a need for an apparatus and method of inversion of multiple echo trains of NMR data. Such a method should be robust and efficient. The present invention satisfies this need.

SUMMARY OF THE INVENTION

One embodiment of the present invention is a method of characterizing an earth formation having a fluid therein. The method includes obtaining a plurality of nuclear magnetic resonance (NMR) echo trains, each of the echo trains resulting from pulsing of the earth formation with an associated pulse sequence having an associated wait time. A plurality of bins of a $T_2$ distribution of the earth formation is defined. For each of the plurality of echo trains, an associated cutoff time for full polarization is determined, and a value associated with each of the plurality of bins is determined based at least in part on the plurality of echo trains and the associated cutoff time. At least one of NMR echo trains may be a fully polarized echo train. The echo trains may be fully polarized echo trains, a clay bound water echo train, or a bulk volume irreducible echo train. Each of the associated cutoff times may be determined from a wait time of the associated pulse sequence and a maximum longitudinal relaxation time of the earth formation. A least squares inversion may be performed. The inversion may be a weighted inversion. Determination of the value associated with each of the plurality of bins involves a simultaneous fitting over each of the echo trains for a bin that is fully polarized for each of the plurality of echo trains and may further involve a simultaneous fitting of a subset of the echo trains for a bin that is fully polarized for the subset of echo trains. At least one characteristic of the earth formation selected from (i) clay bound water, (ii) bulk volume irreducible, and, (iii) porosity may be determined.

Another embodiment of the present invention is an apparatus for characterizing an earth formation having a fluid therein. The apparatus includes a nuclear magnetic resonance (NMR) tool conveyed in a borehole in the earth formation. The NMR tool pulses the earth formation with a plurality of radio frequency (RF) magnetic pulse sequences and receives a plurality of associated echo trains. A processor determines from the plurality of echo trains a value associated with each of a plurality of bins of a $T_2$ distribution, the determination being based at least in part on cutoff times for full polarization associated with each of the plurality of echo trains. The echo trains may be a fully polarized echo trains, a clay bound water echo trains or a BVI echo train. The associated cutoff times may be determined from a wait time of the associated pulse sequence and a maximum longitudinal relaxation time of the earth formation. The processor may determine the value associated with each of the plurality of bins by further performing a least squares inversion. The inversion may be a weighted inversion. The inversion may involve a simultaneous fitting over each of the echo trains for a bin that is fully polarized for each of the plurality of echo trains and may further involve a simultaneous fitting of a subset of the echo trains for a bin that is fully polarized for the subset of echo trains. The processor may be at a surface location, a downhole location, or a remote location. The NMR tool may be conveyed in the borehole on a wireline, a drillstring, or coiled tubing. The processor may determine a characteristic of the earth formation such as clay bound water, bulk volume irreducible, and porosity.

Another embodiment of the present invention is a machine readable medium for use with an apparatus for characterizing an earth formation having a fluid therein. The medium includes instructions that enable a nuclear magnetic resonance (NMR) tool conveyed in a borehole to acquire a plurality of echo trains. The echo trains result from pulsing of the earth formation by an associated pulse sequence that has a wait time. The instructions also enable determination from the plurality of echo trains a value associated with each of a plurality of bins of a $T_2$ distribution. The determination is based at least in part on cutoff times for full polarization associated with each of the plurality of echo trains. The instructions enable the processor to process a fully polarized echo train, a CBW echo train, and a BVI echo train. The instructions further enable performing a least squares inversion. The machine readable medium may be a ROM, an EPROM, an EAROMs, a Flash Memory, or an optical disk. The instructions may further enable determination of a characteristic of the formation such as clay bound water, bulk volume irreducible, or porosity.

BRIEF DESCRIPTION OF THE FIGURES

The present invention is best understood with reference to the accompanying figures in which like numerals refer to like elements and in which.

DETAILED DESCRIPTION OF THE INVENTION

Figure 2:
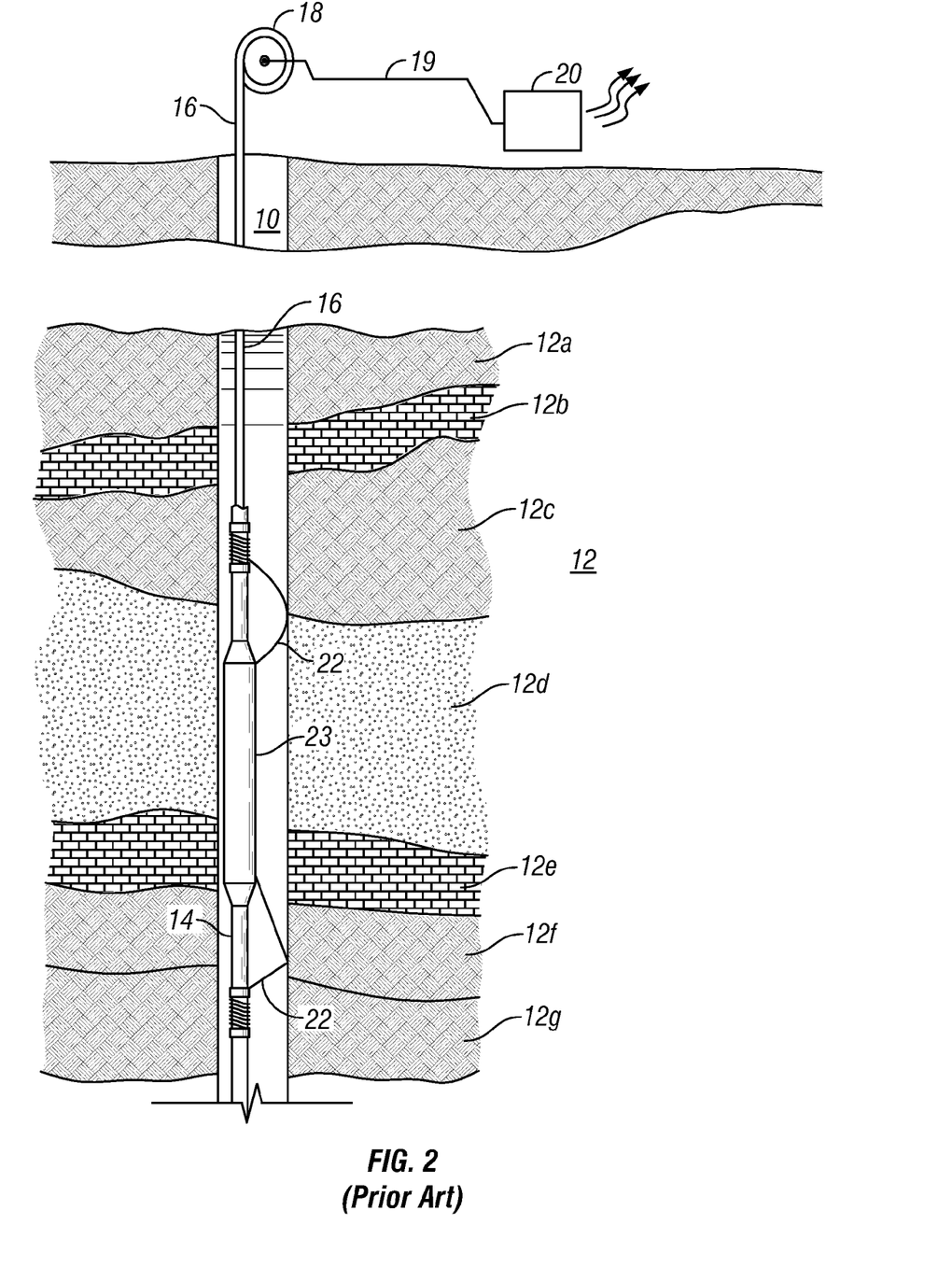
FIG. 2 (prior art) depicts diagrammatically a NMR logging tool conveyed in a borehole in an earth formation FIG. 3 (prior art) show configurations of magnets, antenna and shield of a multifrequency NMR logging tool suitable for use with the present invention.

FIG. 2 depicts a borehole 10 which has been drilled in a typical fashion into a subsurface geological formation 12 to be investigated for potential hydrocarbon producing reservoirs. An NMR logging tool 14 suitable for use with the present invention has been lowered into the hole 10 by means of a cable 16 and appropriate surface equipment represented diagrammatically by a reel 18 and is being raised through the formation 12 comprising a plurality of layers 12a through 12g of differing composition, to log one or more of the formation's characteristics. The NMR logging tool is provided with bowsprings 22 to maintain the tool in an eccentric position within the borehole with one side of the tool in proximity to the borehole wall. The permanent magnets used for providing the static magnetic field are indicated by 23 and the magnet configuration is that of a line dipole. Signals generated by the tool 14 are passed to the surface through the cable 16 and from the cable 16 through another line 19 to appropriate surface equipment 20 for processing, recording and/or display or for transmission to another site for processing, recording and/or display.

Figure 3:
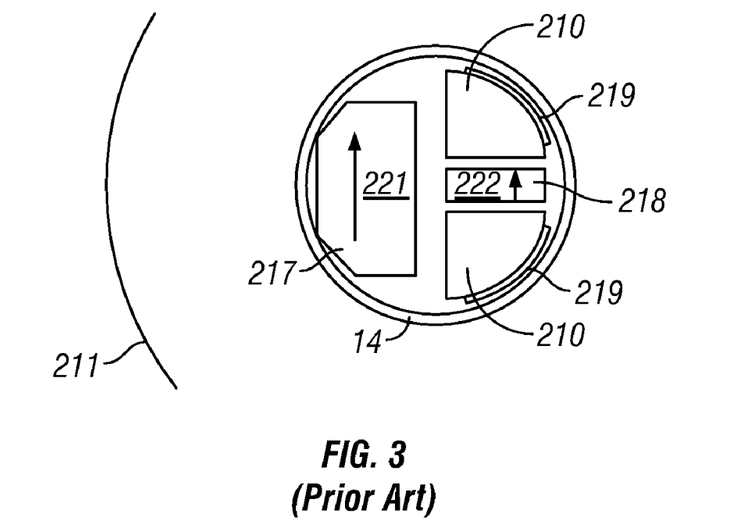

FIG. 3 schematically illustrates a preferred embodiment of the present invention wherein this shaping of the static and RF fields is accomplished. The tool cross-sectional view in FIG. 3 illustrates the tool 14, a main magnet 217, a second magnet 218, and a transceiver antenna, comprising wires 219 and core material 210. The arrows 221 and 222 depict the polarization (e.g., from the South pole to the North pole) of the main magnet 217 and the secondary magnet 218. A noteworthy feature of the arrangement shown in FIG. 3 is that the polarization of the magnets providing the static field is towards the side of the tool, rather than towards the front of the tool (the right side of FIG. 3) as in prior art devices. The importance of this rotated configuration is discussed below.

The second magnet 218 is positioned to augment the shape of the static magnetic field by adding a second magnetic dipole in close proximity to the RF dipole defined by the wires 219 and the soft magnetic core 210. This moves the center of the effective static dipole closer to the RF dipole, thereby increasing the azimuthal extent of the region of examination. The second magnet 218 also reduces the shunting effect of the high permeability magnetic core 210 on the main magnet 217: in the absence of the second magnet, the DC field would be effectively shorted by the core 210. Thus, the second magnet, besides acting as a shaping magnet for shaping the static field to the front of the tool (the side of the main magnet) also acts as a bucking magnet with respect to the static field in the core 210. Those versed in the art would recognize that the bucking function and a limited shaping could be accomplished simply by having a gap in the core; however, since some kind of field shaping is required on the front side of the tool, in a preferred embodiment of the invention, the second magnet serves both for field shaping and for bucking. If the static field in the core 210 is close to zero, then the magnetostrictive ringing from the core is substantially eliminated. FIG. 3 further shows a shield 211.

Additional details of the logging tool and the field shaping are disclosed in U.S. Pat. No. 6,348,792 of Beard et al., having the same assignee as the present invention and the contents of which are fully incorporated herein by reference. As discussed in Beard, within the region of investigation, the static field gradient is substantially uniform and the static field strength lies within predetermined limits to give a substantially uniform Larmor frequency. Those versed in the art would recognize that the combination of field shaping and bucking could be accomplished by other magnet configurations than those shown in FIG. 3.

The NMR instrument described above makes measurements of nuclear spin characteristics of a portion of the earth formation. The magnet arrangement produces a static magnetic field that is spatially varying, particularly as a function of distance from the instrument into the earth formation. The instrument is thus suited for making simultaneous measurements from a plurality of regions, each region characterized by a different field strength (and Larmor frequency) and field gradient. It is to be noted that by using a field shifting magnet, it is also possible to make measurements from the same region at different frequencies.

Figure 4:
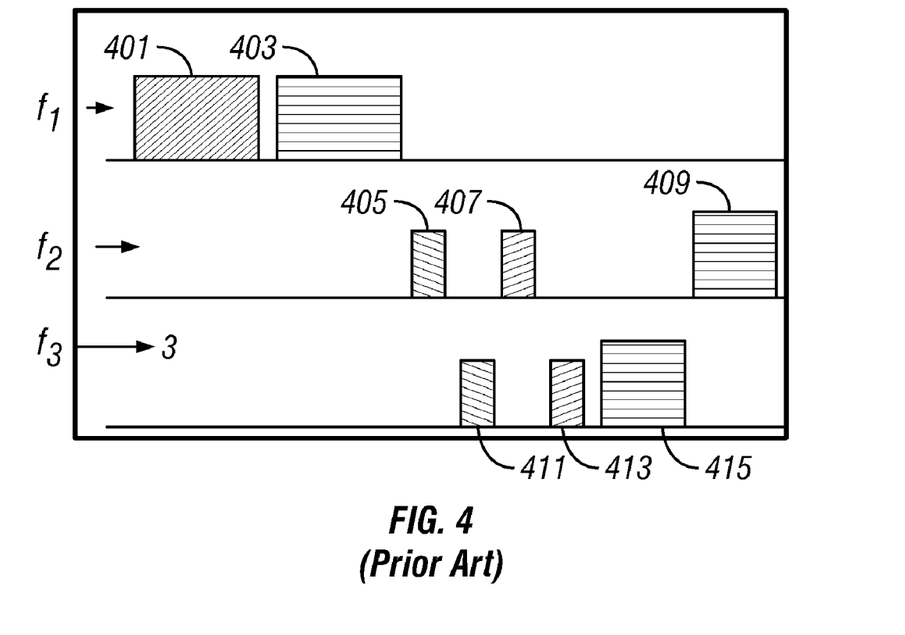
FIG. 4 (prior art) is an example of a NMR pulse sequence at three frequencies.

Turning now to FIG. 4, an example of a three frequency acquisition is shown. The block 401 represents a single CPMG sequence (or modified CPMG sequence with shortened refocusing pulse) at a first frequency $f_1$. This sequence has a typically $TE_1$ range from 0.2-1.0 ms with a total length of 0.5-1.0 s. The block 403 represents a series of trainlets with a $TE_2$ being the shortest possible value by the instrument, usually in 0.2-0.5 ms range, $NE_2*TE_2 \sim 8$ ms, $TW \sim 30$ ms, and number of trainlets $NS \gg 1$. This is acquired at the same frequency as block 401 and the phase is alternated between successive trainlets. This is referred to hereafter as a trainlet sequence. The block 405 at a second frequency $f_2$ comprises a short CPMG (or modified CPMG) sequence with $TE_3$ preferably selected to be the same as $TE_1$, $NE_3*TE_3 \sim 40$ ms, that are fully polarized. This is referred to hereafter as a short sequence. The block 407 at the second frequency $f_2$ comprises a short sequence similar to 405 with $TE_3$ and identical acquisition length $NE_3*TE_3 \sim 40$ ms, that are only partially polarized (Note the short wait time between the end of 405 and the beginning of 407) and that has a phase that is reversed relative to the phase of 405. The next component at the second frequency $f_2$ is the block 409 that is similar to block 403 but does not necessarily contain same number of trainlets, NS. Moving to the third frequency $f_3$, shown are blocks 411 and 413 that are similar to 405 and 407, respectively (i.e., short CPMG sequences with a long and short wait time respectively, polarity flipped between 411 and 413) and a block 415 similar to 409. It should be noted that this is merely an example of the variety of pulse sequences that may be processed using the method of the present invention and is not intended to be a limitation.

In the inversion process, the inversion involves finding amplitudes $\{x_i\}$ such that $$d(t_j) = \sum_{i=1}^{M} x_i e^{-t_j/T_{2i}}, \qquad (2)$$

where $d(t_j)$ is the echo amplitude at time $t_j$, and $\{T_{2i}\}$ are the relaxation times associated with the $\{x_i\}$. There are N echoes and M relaxation components. In matrix notation $$d = Ax, \qquad (3),$$

where d is an N×1 column vector; A is an N×M matrix; and x is an M×1 column matrix. The column vector, T, contains the corresponding relaxation times for the amplitudes in x.

$$T = (T_{21}, T_{22}, \ldots, T_{2M})^T$$

The elements of A are computed as $$A_{i,j} = e^{-t_i/T_{2j}} \qquad (4).$$

The inversion involves minimization of $$\sigma^2 = (Ax-d)^T W(Ax-d) + \alpha x^T W_m x, \qquad (5),$$

where W is a data weighting matrix and $W_m$ is a regularization matrix representing are prior knowledge about the result x, and α is the regularization parameter. The resulting expression for x is $$0 = A^T W A x + \alpha W_m x - A^T W d \qquad (6).$$

This expression can be solved using many different methods from conventional inversion to singular value decomposition. The weighting matrices are chosen to be any that satisfy the problem and a priori knowledge of the problem we are trying to solve.

Separate inversion solves two or more of the above expressions. Joint inversion concatenates two or more of the above expressions. If two echo trains are to be inverted, then the concatenation/minimization may be represented by $$A = \begin{bmatrix} A_1 \\ A_2 \end{bmatrix}; W = \begin{bmatrix} W_1 & 0 \\ 0 & W_2 \end{bmatrix}; d = \begin{bmatrix} d_1 \\ d_2 \end{bmatrix}. \qquad (7)$$

For additional echo trains, the expressions are easy to generalize. For partially polarized amplitudes where the TW are small, $$A_{(1,2)i,j} = e^{-t_i/T_{2j}}(1 - e^{-TW_{(1,2)}/rT_{2j}}) \qquad (8).$$

In the present invention, the simultaneous problem is solved with M independent amplitudes. A different subset of these amplitudes is used to fit the each one of the echo trains. The $T_2$ for each amplitude does not necessarily need to be unique. One echo train might use an amplitude with a $T_2$ of 64 msec and a different amplitude is used for a different echo train but with the same $T_2$ of 64 msec. Let the vector of independent amplitudes be x. Then we can map the subset of $x_i$ used for each echo train by a mapping matrix.

$$x_i = M_i x, \qquad (9),$$

where $x_i$ is a $M_i \times 1$ column matrix and $M_i$ is a $M_i \times M$ with only a single one in each row that corresponds to an amplitude in the $i^{th}$ subspace and zeros elsewhere. In addition, $M_i \leq M$. The column vector T contains the corresponding relaxation times $$T = (T_{2,1}, T_{2,2}, \ldots, T_{2,M})^T.$$

Substituting from eqn. (9) into eqn. (5) gives $$\sigma^2 = \sum_i (A_i x_i - d_i)^T W_i (A_i x_i - d_i) + \alpha_i x_i^T W_{m,i} x_i, \qquad (10)$$

$$= \sum_i (A_i M_i x - d_i)^T W_i (A_i M_i x - d_i) + \alpha_i (M_i x)^T W_{m,i} M_i x.$$

Each $A_i$ is an $N_i \times M_i$ matrix where each echo train has $N_i$ echoes. It has elements $$(A_k)_{i,j} = e^{-t_i/(T_k)_j} \qquad (11),$$

where the relaxation times are taken from the vector $$T_k = M_k T. \qquad (12).$$

Taking the derivative of eqn. (10) with respect to x results in an equation that can be solved for the amplitudes:

$$\sum_i M_i^T A_i^T W_i d_i = \left[ \sum_i (M_i^T A_i^T W_i A_i M_i + \alpha_i M_i^T W_{m,i} M_i) \right] x. \qquad (13)$$

This can be further simplified by setting $$A'_i = A_i M_i \qquad (14),$$

and $$W'_{m,i} = M_i^T W_{m,i} M_i \qquad (15).$$

Eqn. (13) then becomes $$\sum_i A_i'^T W_i d_i = \left[ \sum_i (A_i'^T W_i A_i' + \alpha_i W'_{m,i}) \right] x. \qquad (16)$$

Eqn. (16) can be inverted using prior art methods.

A specific example is given to illustrate the multiple echo train inversion and the structure of the various matrices. The acquisition parameters for a three-frequency acquisition are shown in Table 1.

TABLE 1

Echo1 is the long T2 echo train. It is fully polarized. Echo2 is echo train from the CBW trainlets. Echo3 is the bound water echo trains. The bin times are $2^{(2n-3)/2}$

| Parameter | Echo1 | Echo2 | Echo3 | Units |
|---|---|---|---|---|
| NE | 833 | 16 | 83 | |
| TE | 0.6 | 0.6 | 0.6 | Ms |
| NA | 1 | 50 | 4 | |
| TW | Fully polarized | 30 | 100 | Ms |
| Noise | 2 | 0.28 | 1 | Pu |
| Bins | $2^{(-1,1,3,\ldots 11)}$ | $2^{(-1,1,3,\ldots 7)}$ | $2^{(-1.5,-1,0,\ldots 9)}$ | |

All the relaxation components in Echo1 are fully polarized. Only some of the components in Echo2 and Echo3 are fully polarized. We seek to fit the echo trains with amplitudes that have the bin times given in the table. The bin times are $2^{(2n-3)/2}$ ms where n is a positive integer.

The amplitudes to be fit simultaneously are found by comparing the polarization of each amplitude. The CBW trainlets (Echo2) have the smallest TW and therefore the fewest components are fully polarized. Thus, the relaxation times for those components must satisfy $$T_2 \leq \frac{TW}{1.5 \cdot 3}. \tag{17}$$

Here, the factor 1.5 is the $T_1/T_2$ ratio and it is assumed that $TW > 3T_1$ to be fully polarized. As noted above, this ratio is not a limitation to the present invention and can be different for the different echo trains. For this particular case TW is the minimum TW and corresponds to the CBW echo trainlets or Echo2. The cutoff value is 6.67. Therefore the components with $T_2 < 6.67$ msec for all echo trains are fully polarized and a common set of partial porosities is used to fit these components. The remainder of the components that fit Echo2 are not fully polarized and require independent amplitudes.

To find the amplitudes that are common between Echo1 and Echo3 we simply substitute the TW of Echo3 or the BW echo trains. The cutoff is 22.2 ms for Echo3. Thus components with $6.67 < T_2 < 22.2$ ms use a common set of partial porosities to fit both Echo1 and Echo3. The remainder of components with $T_2 > 22.2$ ms that fit Echo3 are not fully polarized and the partial porosities are independent. The remainder of the components that fit Echo1 are fully polarized and fit with independent partial porosities. To obtain the fully polarized T2 spectrum we take the fully polarized independent amplitudes. These amplitudes fit Echo1.

Echo1 is fit by 7 amplitudes, Echo2 is fit by 4 amplitudes, and Echo3 is fit by 5 amplitudes. The total number of amplitudes is 16, but only 11 are independent. The bin time vector becomes $$T = (0.5, 2, 8, 32, 128, 512, 2048, 8, 32, 32, 128)^T \tag{18}.$$

The mapping matrices are:

$$M_1 = \begin{pmatrix} 1 & 0 & 0 & 0 & 0 & 0 & 0 & 0 & 0 & 0 & 0 \\ 0 & 1 & 0 & 0 & 0 & 0 & 0 & 0 & 0 & 0 & 0 \\ 0 & 0 & 1 & 0 & 0 & 0 & 0 & 0 & 0 & 0 & 0 \\ 0 & 0 & 0 & 1 & 0 & 0 & 0 & 0 & 0 & 0 & 0 \\ 0 & 0 & 0 & 0 & 1 & 0 & 0 & 0 & 0 & 0 & 0 \\ 0 & 0 & 0 & 0 & 0 & 1 & 0 & 0 & 0 & 0 & 0 \\ 0 & 0 & 0 & 0 & 0 & 0 & 1 & 0 & 0 & 0 & 0 \end{pmatrix}. \tag{19}$$

$$M_2 = \begin{pmatrix} 1 & 0 & 0 & 0 & 0 & 0 & 0 & 0 & 0 & 0 & 0 \\ 0 & 1 & 0 & 0 & 0 & 0 & 0 & 0 & 0 & 0 & 0 \\ 0 & 0 & 0 & 0 & 0 & 0 & 0 & 1 & 0 & 0 & 0 \\ 0 & 0 & 0 & 0 & 0 & 0 & 0 & 0 & 1 & 0 & 0 \end{pmatrix}$$

$$M_3 = \begin{pmatrix} 1 & 0 & 0 & 0 & 0 & 0 & 0 & 0 & 0 & 0 & 0 \\ 0 & 1 & 0 & 0 & 0 & 0 & 0 & 0 & 0 & 0 & 0 \\ 0 & 0 & 1 & 0 & 0 & 0 & 0 & 0 & 0 & 0 & 0 \\ 0 & 0 & 0 & 0 & 0 & 0 & 0 & 0 & 0 & 1 & 0 \\ 0 & 0 & 0 & 0 & 0 & 0 & 0 & 0 & 0 & 0 & 1 \end{pmatrix}$$

The elements of the forward models are $$(A_1)_{i,j} = e^{-iTE_1/(T^1)_j}(T^1)_j \in \{0.5, 2, 8, 32, 128, 512, 2048\} i \in \{1,2,3,\ldots, NE_1\} \tag{20},$$

$$(A_2)_{i,j} = e^{-iTE_2/(T^2)_j}(T^2)_j \in \{0.5, 2, 8, 32\} i \in \{1,2,3,\ldots, NE_2\} \tag{21},$$

and $$(A_3)_{i,j} = e^{-iTE_3/(T^3)_j}(T^3)_j \in \{0.5, 2, 8, 32, 128\} i \in \{1,2,3,\ldots, NE_3\} \tag{22}.$$

In eqns. (20)-(22), a superscript has been used to avoid any possible confusion with actual longitudinal and transverse relaxation times. The largest time in eqn (20)-(22) is at least as long as the pulse sequence. Note that the elements of eqn. (18) are:
  (i) all the elements of the times from eqn. (20),
  (ii) the elements of the times from eqn. (21) that exceed the cutoff time of 6.67 ms, and
  (iii) the elements of the times from eqn. (22) that exceed the cutoff time of 22.2 ms.

The weighting matrices are $NE_i \times NE_i$ diagonal matrices with values $$W = \frac{1}{\sigma_e^2} \begin{bmatrix} \sigma_e^2/\sigma_1^2 & & & & \\ & 1 & & & \\ & & \ddots & & \\ & & & \ddots & \\ & & & & 1 \end{bmatrix}, \tag{23}$$

where $\sigma_1$ is the noise on the first echo and $\sigma_e$ is the noise on the remainder of the echoes. In our case the ratio is $\sigma_1/\sigma_e = 1.6$. The regularization matrix minimizes the curvature. The curvature matrices with zero amplitude boundary conditions are $M_i \times M_i$ tridiagonal matrices with values $$C = \begin{bmatrix} -2 & 1 & & & \\ 1 & -2 & 1 & & \\ & \ddots & \ddots & \ddots & \\ & & 1 & -2 & 1 \\ & & & -1 & 2 \end{bmatrix}, \tag{24}$$

$$W_m = C^T C. \tag{25}.$$

The optimum regularization coefficient is given as $$\alpha_i = \sqrt{\frac{(A_i'x - d_i)^T(A_i'x - d_i)}{NE_i(M_i x)^T(M_i x)}}. \tag{26}$$

This result follows from a result in Butler et al., "Estimating Solutions of First Kind Integral Equations with Non-negative Constraints and Optimal Smoothing," SIAM J. Numerical Analysis, vol. 18, no. 3, pp 381-397.

To summarize, in the multiple echo train inversion, an assumption is made that some upper limit exists for the $T_1/T_2$ ratio and is known a priori. There is no assumption that the ratio $T_1/T_2$ is constant. In addition, all the available data are used to compute an optimized total porosity T2 spectrum. The criterion for determining which components are fit simultaneously compares TW to the component's relaxation time. If the component is fully polarized for all the echo trains it is fit simultaneously. If the component is fully polarized for a subset of the echo trains, it is fit simultaneously only to those echo trains. The method uses non-negative least-square formalism to obtain the $T_2$ spectrum. The formalism demonstrates that only an M×M matrix need be inverted, where M is the number of independent amplitudes in the inversion. This matrix is the sum of matrices calculated in the separate inversion process.

Figure 5A:
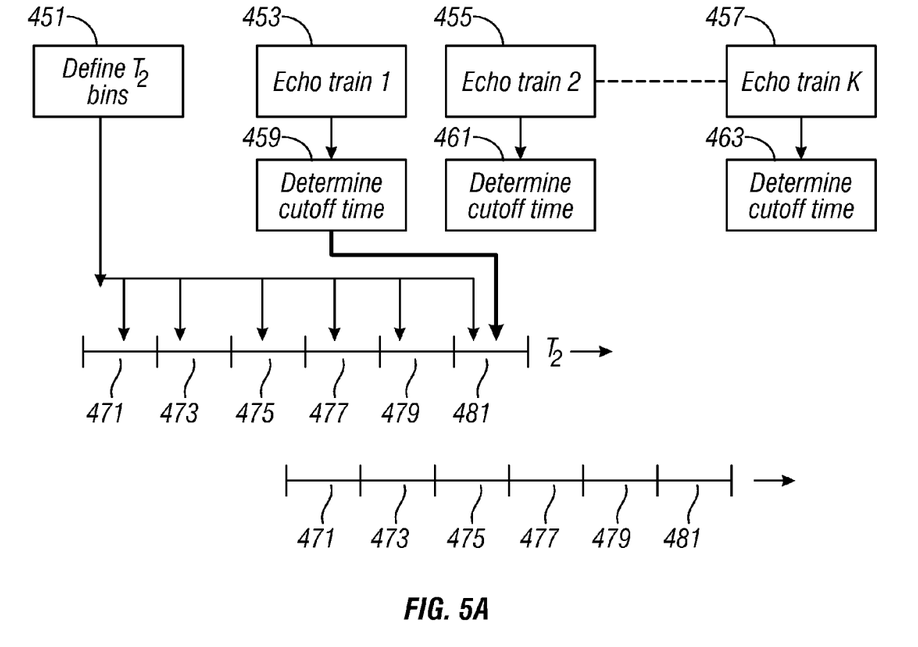
FIGS. 5A and 5B show a flow chart illustrating the method of the present invention.

This is depicted schematically in FIG. 5A. The $T_2$ bins are defined 451 and depicted by 471, 473, 475, 477, 479 and 481. To simplify the illustration, the bins are shown of equal size, but typically they are defined on a logarithmic scale as given by eqn. (18). A plurality of echo trains 453, 455, . . . 457 is acquired. The range of bin sizes for which a $T_2$ distribution may be obtained using the method of the present invention is determined from the characteristics of the individual echo trains. For the example of Table 1, the largest $T_2$ is determined from the time at which the first (fully polarized) echo train amplitude has an acceptable signal to noise ratio. The smallest $T_2$ is controlled by the smallest TE in any of the echo trains.

For echo train 1, a determination of a cutoff time is made 453 using eqn. (17). It should be noted that in eqn. (17), the factor of 1.5 is for exemplary purposes only and other factors could be used based on a priori knowledge. In this regard, the method of the present invention is quite different from prior art methods where a constant ratio of $T_1/T_2$ is assumed. Based on this determined cutoff, echo train 1 is used only for bins 471, 473, 475, 477, 479 and 481. This may be considered as a threshold test for the contribution of echo train to the final inversion. This is repeated for the other echo trains. Thus, for echo train 2 453, the cutoff time is determined at 459, 461, 463 etc.

Figure 5B:
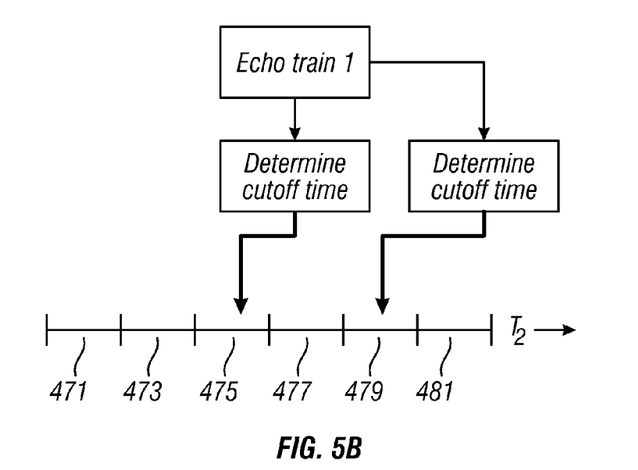

Turning to FIG. 5B, for echo train 2, the cutoff corresponds to bin 475 while the maximum time for echo train 2 corresponds to bin 479. Hence the bin vector for echo train has independent components for bins 475, 477 and 479. This process is repeated for the remaining echo trains.

In the case of the echo trains of Table 1, echo train 1 is fully polarized, hence it will contribute to all bins up to its maximum time. The bin time vector given by eqn. (18) is a concatenation of:
(i) all bins corresponding to the fully polarized echo trains,
(ii) partially polarized bins for echo train 2, i.e, the range between its cutoff time and its maximum time; and
(iii) partially polarized bins for echo train 3, i.e., the range between its cutoff time and its maximum time.

Once the vector T has been defined, the rest is straightforward.

To evaluate the characteristics of the method of the present invention, a synthetic example is shown. Bin times for the fully polarized echo data were (0.35, 0.5, 0.71, . . . , 2048). The bin times for Echo2 were (0.35,0.5,0.71 . . . 128). The bin times for the bound water echo trains or Echo3 were (0.35, 0.5,0.71 . . . 512). The regularization matrix used was the curvature smoothing with zero amplitude boundary conditions. Finally, the synthetic data were constructed using a single exponential such that $$d_{n,j} = 10\exp\{-nTE/T_2\}(1-\exp\{-TW_j/1.5T_2\}) + e_{n,j},$$

where j represents the echo train number. The $e_{n,j}$ are noise amplitudes randomly generated from Gaussian distributions with RMS widths of (2, 0.28, 1) for echo train j. $T_2$ was varied from 0.1 to 1000 ms. One hundred different instances of the echo trains were generated for each $T_2$ in order to compute statistical measures of the inversion results.

Figure 6:
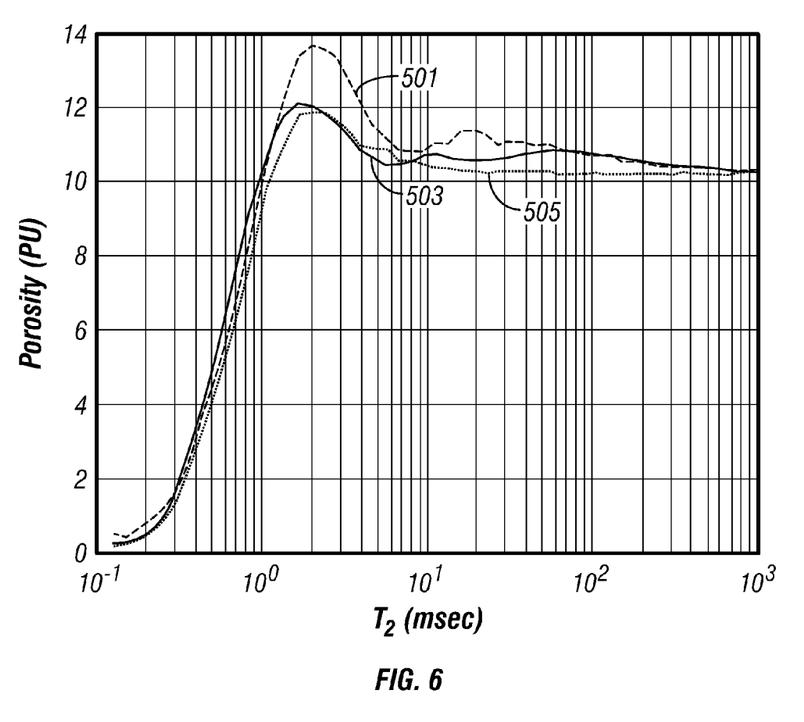
FIG. 6 shows an exemplary comparison of a $T_2$ distribution obtained using the method of the present invention with results obtained using prior art methods on a set of synthetic examples.

Shown in FIG. 6 are the total porosity estimates 503 using the method of the present invention. The curve 501 is the result of separately inverting the three echo trains and splicing the results. The curve 505 is another prior art method referred to as a joint inversion. The Joint Inversion method uses a common set of partial porosities to invert the echo trains simultaneously. The difference in the polarization of the echo trains is accounted for by multiplying each partial porosity by a polarization factor. Because the polarization factor depends on $T_1$ instead of $T_2$, a new parameter is introduced call the $T_1/T_2$ ratio. The $T_1/T_2$ ratio is optimized along with the partial porosities. Unlike the Separate Inversion method, it produces a smooth $T_2$ distribution. However, the limitation to the joint inversion method is the assumption that the $T_1/T_2$ ratio is constant. For core plugs, the $T_1/T_2$ ratio varies from about 1 to more than 3. It should be expected that this ratio will vary within the sensitive volume of an NMR logging tool.

Figure 7:
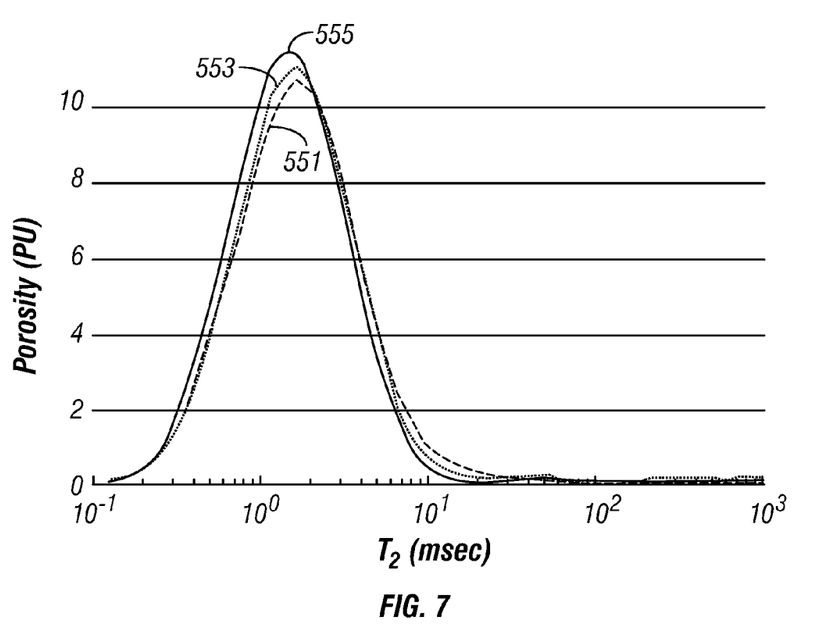
FIG. 7 shows an exemplary comparison of the CBW distribution obtained using the method of the present invention with results obtained using prior art methods on a set of synthetic examples.

Still with reference to the synthetic model, FIG. 7 shows the CBW estimate for the separate inversion 551, the multiple echo-train inversion of the present method 553 and the joint inversion 555. The three echo train inversion CBW estimate has improved characteristics at 0.5 ms and goes to zero above 4 ms faster than the separate or joint inversion. Having the complete $T_2$ distribution enables determination of CBW, BVI and porosity.

An alternate embodiment of the invention starts with the same cost function as that given by eqn. (5):

$$\sigma^2 = (Ax-d)^T W(Ax-d) + \alpha x^T W_m x, \qquad (27)$$

where $$A_{i,j} = e^{-\frac{t_i}{T_{2,j}}}. \qquad (28)$$

Now suppose that we want to use the same coefficient for multiple inversions. The fully polarized components are included in all the inversions. Thus, any bin time less than 3*TW is included all inversions. Thus, bins of the $T_2$ distribution for which $T_{2,i} \leq 4$ ms are included in the CBW, BVI, and FP inversions. Bins of the $T_2$ distribution for which $4 < T_{2,i} \leq 16$ ms are included in the BVI and FP inversions. Finally, only those bins larger than 16 ms are included in the FP inversion. Also important is the notion, that to completely fit the partially polarized data we need to include bins for the partially polarized part of the echoes. Thus $$T_{2cbw,i} = \{0.35, 0.5, \ldots, 4, 5.6, \ldots, 256\}$$

$$T_{2bvi,i} = \{0.35, 0.5, \ldots, 16, 22.6, \ldots, 256\}$$

$$T_{2fp,i} = \{0.35, 0.5, \ldots, 2048\}$$

and $$x_i = \{x_{0.35}, \ldots, x_{2048}, x_{bvi,22.6}, \ldots, x_{bvi,256}, x_{cbw,5.6}, \ldots, x_{cbw,256}\}$$

$$T_{2,i} = \{0.35, \ldots, 2048, 22.6, \ldots, 256, 5.6, \ldots, 256\}$$

$$t_i = \{t_{fp,1}, \ldots, t_{fp,N_{fp}}, t_{bvi,1}, \ldots, t_{bvi,N_{bvi}}, t_{cbw,1}, \ldots, t_{cbw,N_{cbw}}\}$$

Those labeled with CBW and BVI are used only to fit the data from those echo trains and discarded. The final product are the unlabeled bins. Let $x_1$ to $x_J$ be the final product and let $x_{J+1}$ to $x_{J+K}$ be those fit only to the BVI echo train and $x_{J+K+1}$ to $x_{J+K+L}$ be fit only to the CBW echo trains. Thus the A matrix becomes $$A = \left\{ \begin{array}{ccc|ccc|ccc}
e^{-t_1/T_{2,1}} & \cdots & e^{-t_1/T_{2,1}} & & & & & & \\
\vdots & \ddots & \vdots & & 0 & & & 0 & \\
e^{-t_{N_{fp}}/T_{2,1}} & \cdots & e^{-t_{N_{fp}}/T_{2,1}} & & & & & & \\
\hline
e^{-t_{N_{fp}+1}/T_{2,1}} & \cdots & e^{-t_{N_{fp}+1}/T_{2,J_{bvi}}} & e^{-t_{N+1}/T_{2,J+1}} & \cdots & e^{-t_{N+1}/T_{2,J+K}} & & & \\
\vdots & \ddots & \vdots & \vdots & \ddots & \vdots & & 0 & \\
e^{-t_{N_{bvi}+N_{fp}}/T_{2,1}} & \cdots & e^{-t_{N_{bvi}+N_{fp}}/T_{2,J_{bvi}}} & e^{-t_{N_{bvi}+N_{fp}}/T_{2,J+1}} & \cdots & e^{-t_{N_{bvi}+N_{fp}}/T_{2,J+K}} & & & \\
\hline
e^{-t_i/T_{2,1}} & \cdots & e^{-t_i/T_{2,J_{cbw}}} & e^{-t_{N_{bvi}+N_{fp}+1}/T_{2,J+1}} & \cdots & e^{-t_{N_{bvi}+N_{fp}+1}/T_{2,J+K}} & e^{-t_{N_{bvi}+N_{fp}+1}/T_{2,J+K+1}} & \cdots & e^{-t_{N_{bvi}+N_{fp}+1}/T_{2,J+K+L}} \\
\vdots & \ddots & \vdots & \vdots & \ddots & \vdots & \vdots & \ddots & \vdots \\
e^{-t_{N_{cbw}+N_{bvi}+N_{fp}}/T_{2,1}} & \cdots & e^{-t_{N_{cbw}+N_{bvi}+N_{fp}}/T_{2,J_{cbw}}} & e^{-t_{N_{cbw}+N_{bvi}+N_{fp}}/T_{2,J+1}} & \cdots & e^{-t_{N_{cbw}+N_{bvi}+N_{fp}}/T_{2,J+K}} & e^{-t_{N_{cbw}+N_{bvi}+N_{fp}}/T_{2,J+K+1}} & \cdots & e^{-t_{N_{cbw}+N_{bvi}+N_{fp}}/T_{2,J+K+L}}
\end{array} \right.$$

$$A = \left\{ \begin{array}{c|c|c}
[N_{fp} \times J] & 0 & 0 \\
\hline
[N_{bvi} \times J_{bvi}] & [N_{bvi} \times K] & 0 \\
\hline
[N_{cbw} \times J_{cbw}] & 0 & [N_{cbw} \times L]
\end{array} \right.$$

Constraints such as minimum norm or curvature may be added. The minimum norm matrix for a single inversion is given by $$W_m = \begin{pmatrix} 1 & 0 & & & & & \\ 0 & 1 & 0 & & & & \\ & 0 & 1 & 0 & & & \\ & & \ddots & \ddots & \ddots & & \\ & & & 0 & 1 & 0 & \\ & & & & 0 & 1 & 0 \\ & & & & & 0 & 1 \end{pmatrix}$$

This could be used straightforwardly. Different weighting factors could be applied to those coefficients that are used in the fit of more than one echo train. The curvature smoothing constraint is less easy. For zero amplitude boundary conditions, $$C = \begin{pmatrix} -2 & 1 & & & & & \\ 1 & -2 & 1 & & & & \\ & 1 & -2 & 1 & & & \\ & & \ddots & \ddots & \ddots & & \\ & & & 1 & -2 & 1 & \\ & & & & 1 & -2 & 1 \\ & & & & & 1 & -2 \end{pmatrix}$$

$$W_m = C^T C$$

The regularization conditions need to be kept separate because they are squared before they are summed. Thus we get to solve this equation $$\left( \sum_i \alpha_i W_{m,i} + A^T W A \right) x = A^T W d$$

The processing of the measurements made by the probe in wireline applications may be done by the surface processor 20 or may be done by a downhole processor (not shown). For MWD applications, the processing may be done by a downhole processor that is part of a bottomhole assembly BHA conveyed on a tubular such as a drillstring or coiled tubing. This downhole processing reduces the amount of data that has to be telemetered. Alternatively, some or part of the data may be telemetered to the surface. In yet another alternative, the measurements may be stored on a suitable memory device downhole and processed when the drillstring is tripped out of the borehole. Part of the processing may also be done at a remote location.

The operation of the NMR sensor may be controlled by the downhole processor and/or the surface processor. Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

While the foregoing disclosure is directed to the specific embodiments of the invention, various modifications will be apparent to those skilled in the art. It is intended that all such variations within the scope and spirit of the appended claims be embraced by the foregoing disclosure.

The invention claimed is:

1. A method of characterizing an earth formation, the method comprising:
   (a) obtaining a plurality of nuclear magnetic resonance (NMR) echo trains;
   (b) defining a plurality of bins of a T2 distribution of the earth formation; and
   (c) for each of the plurality of echo trains, determining an associated cutoff time for full polarization; and
   (d) determining a value associated with each of the plurality of bins based at least in part on the plurality of echo trains and the associated cutoff time.

2. The method of claim 1 wherein at least one of NMR echo trains is a fully polarized echo train.

3. The method of claim 1 wherein the plurality of echo trains are selected from the group consisting of (i) a fully polarized echo train, (ii) a CBW echo train, and, (iii) a BVI echo train.

4. The method of claim 1 wherein each of the associated cutoff times is determined from a wait time of an associated pulse sequence and a maximum longitudinal relaxation time of the earth formation.

5. The method of claim 1 wherein determining the value associated with each of the plurality of bins further comprises performing a least squares inversion.

6. The method of claim 5 wherein the inversion comprises a weighted inversion.

7. The method of claim 1 wherein determining the value associated with each of the plurality of bins further comprises a simultaneous fitting over each of the echo trains for a bin that is fully polarized for each of the plurality of echo trains.

8. The method of claim 1 wherein determining the value associated with each of the plurality of bins further comprises a simultaneous fitting of a subset of the echo trains for a bin that is fully polarized for the subset of echo trains.

9. The method of claim 2 wherein determining the value associated with each of the plurality of bins further comprises defining a vector that includes bins associated with the fully polarized echo train and a partially polarized bin for at least one other echo train.

10. The method of claim 1 further comprising determining at least one characteristic of the earth formation selected from (i) clay bound water, (ii) bulk volume irreducible, and, (iii) porosity.

11. An apparatus for characterizing an earth formation the apparatus comprising:
   (a) a nuclear magnetic resonance (NMR) tool configured to be conveyed in a borehole in the earth formation, the NMR tool configured to pulse the earth formation with a plurality of radio frequency (RF) magnetic pulse sequences and receive a plurality of associated echo trains;
   (b) a processor configured to:
      determine from the plurality of echo trains a value associated with each of a plurality of bins of a $T_2$ distribution, the determination based at least in part on cutoff times for full polarization associated with each of the plurality of echo trains.

12. The apparatus of claim 11 wherein the plurality of echo trains are selected from the group consisting of (i) a fully polarized echo train, (ii) a CBW echo train, and, (iii) a BVI echo train.

13. The apparatus of claim 11 wherein each of the associated cutoff times is determined from a wait time of the associated pulse sequence and a maximum longitudinal relaxation time of the earth formation.

14. The apparatus of claim 11 wherein the inversion comprises a weighted inversion.

15. The apparatus of claim 11 wherein the processor is configured to determine the value associated with each of the plurality of bins by performing a simultaneous fitting over each of the echo trains for a bin that is fully polarized for each of the plurality of echo trains.

16. The apparatus of claim 11 wherein the processor is configured to determine the value associated with each of the plurality of bins by performing a simultaneous fitting of a subset of the echo trains for a bin that is fully polarized for the subset of echo trains.

17. The apparatus of claim 11 wherein the processor is configured to determine the value associated with each of the plurality of bins by defining a vector that includes bins associated with a fully polarized echo train and a partially polarized bin for at least one other echo train.

18. The apparatus of claim 11 wherein the processor is configured to be deployed at a location selected from the group consisting of (i) a surface location, (ii) a downhole location, and, (iii) a remote location.

19. The apparatus of claim 11 further comprising a conveyance device configured to convey the NMR tool into the borehole, the conveyance device selected from the group consisting of: (i) a wireline, (ii) a drillstring, and, (iii) coiled tubing.

20. The apparatus of claim 11 wherein the processor is further configured to determine a characteristic of the earth formation selected from (i) clay bound water, (ii) bound volume irreducible, and, (iii) porosity.

21. A computer readable medium having stored thereon instructions that when read by at least one processor enable the at least one processor to perform a method, the method comprising:

simultaneously inverting a plurality of echo trains acquired using a nuclear magnetic resonance (NMR) tool conveyed in a borehole, each of the echo trains resulting from pulsing of an earth formation with an associated pulse sequence having an associated wait time, determining from the plurality of echo trains a value associated with each of a plurality of bins of a $T_2$ distribution, and recording the determined value on a suitable medium.

22. The computer readable medium of claim 21 wherein the medium is selected from the group consisting of (i) a ROM, (ii) an EPROM, (iii) an EAROM, (iv) a flash memory, and (v) an optical disk.

* * * * *